United States Patent [19]

Nishihira et al.

[11] Patent Number: 5,214,185
[45] Date of Patent: May 25, 1993

[54] CONTINUOUS PROCESS FOR PREPARING DIMETHYL CARBONATE

[75] Inventors: Keigo Nishihira; Shin-ichi Yoshida; Shuji Tanaka, all of Ube, Japan

[73] Assignee: Ube Industries, Ltd., Yamaguchi, Japan

[21] Appl. No.: 914,355

[22] Filed: Jul. 17, 1992

[30] Foreign Application Priority Data

Jul. 19, 1991 [JP] Japan ................ 3-269950
Jul. 19, 1991 [JP] Japan ................ 3-269951

[51] Int. Cl.$^5$ ............................. C07C 69/96
[52] U.S. Cl. ..................... 558/277; 558/260; 558/270; 558/274; 558/276
[58] Field of Search .......................... 558/277

[56] References Cited

U.S. PATENT DOCUMENTS 4,929,748  5/1990  Franklin ...................... 558/277
5,142,086  8/1992  King, Jr. et al. ............. 558/277

Primary Examiner—Johann Richter
Attorney, Agent, or Firm—Finnegan, Henderson, Farabow, Garrett & Dunner

[57] ABSTRACT

Disclosed is a continuous process for preparing dimethyl carbonate which comprises:

a first step of introducing a gas containing carbon monoxide and methyl nitrite into a reactor filled with a solid catalyst to obtain a reaction product containing dimethyl carbonate;

a second step of separating the reaction product to a non-condensed gas and a solution containing dimethyl carbonate by adding dimethyl oxalate;

a third step of introducing the non-condensed gas into a regenerating column to contact it with a molecular state oxygen-containing gas and methanol whereby regenerating nitrogen monoxide to methyl nitrite, so as to contain 2 to 7% by volume of nitrogen monoxide in a non-absorbed gas at an outlet of the column, which in turn is introduced in the reactor of the first step;

a fourth step of extracting, distilling and separating dimethyl carbonate from the solution by further adding dimethyl oxalate to remove methanol; and a fifth step of distilling and separating dimethyl carbonate from a mixed solution to remove dimethyl oxalate and recycling the removed dimethyl oxalate to the fourth step.

15 Claims, 1 Drawing Sheet

CONTINUOUS PROCESS FOR PREPARING DIMETHYL CARBONATE

BACKGROUND OF THE INVENTION

This invention relates to a process for continuously preparing dimethyl carbonate which is useful as a synthesis starting material for an aromatic polycarbonate and various chemical products. More particularly, it relates to a process for preparing dimethyl carbonate from carbon monoxide and methyl nitrite in a vapor phase in the presence of a platinum group metal solid catalyst which can be carried out industrially advantageously and separated continuously. Dimethyl carbonate is a compound extremely useful as a starting material for organic syntheses of medicines and agricultural chemicals, and for syntheses of aromatic polycarbonates and urethanes.

In the prior art, as a process for preparing dimethyl carbonate by contacting carbon monoxide and methyl nitrite to a platinum group metal solid catalyst in a vapor phase, the present inventors have proposed, for example, in Japanese Provisional Patent Publication No. 141243/1991 (which corresponds to U S. patent application Ser. No. 07/599, 134 now U.S. Pat. No. 5,162,563 or European Patent Application No. 90 311 469.2) or Japanese Provisional Patent Publication No. 139152/1992. The reaction itself disclosed therein is extremely excellent as a process for preparing dimethyl carbonate. However, in order to apply the reaction to the industries and to effect preparation of dimethyl carbonate to an industrial scale, it is required to develop a process which can conduct the reaction, separation and purification continuously and effectively.

As a process for preparing dimethyl carbonate from carbon monoxide and methyl nitrite, in addition to the process proposed by the present inventors, there has been proposed a process as disclosed in Japanese Provisional Patent Publication No. 181051/1985, but the disclosure is insufficient for using the process as an industrially continuous process.

As a conventional technique, in the process for separating a desired component from a mixed gas, there may be mentioned an absorption method using a solvent, a condensation method by cooling, a method of using an absorbant and a combination of these methods when the desired component has a high boiling point as in the present invention. In addition, there is a specific method such as a membrane separation, but in order to prepare dimethyl carbonate which should be prepared by a mass production with inexpensive using an industrial apparatus, it is required that the industrial apparatus should be simple, advantageous in energy efficiency and economically excellent.

A mixed gas obtained by the reaction disclosed in the aforesaid Japanese Provisional Patent Publication No. 141243/1991 mainly comprises a nitrogen gas, and in addition to dimethyl carbonate, contains carbon monoxide, methyl nitrite, nitrogen monoxide, methanol and a small amount of dimethyl oxalate.

In order to separate dimethyl carbonate and dimethyl oxalate from the mixed gas, the above mentioned methods are used, and of these methods, an absorption separation using methanol has most commonly used. In fact, a certain extent of separation efficiency can be obtained by the method, However, in order to heighten separation efficiency to a level sufficient for an industrial scale, there are inappropriate aspects that cooling is conducted at a significantly low temperature, a separation tower having high step number is required or a separation system should be made significantly high pressure.

Also, when separating dimethyl carbonate by distillation, it forms azeotropic composition with methanol and thus it should be finally separated from methanol. Considering this fact, it is clear that a methanol concentration in a separated material from a reaction gas mixture should preferably be low in view of energy burden. Thus, it cannot be considered that it is appropriate to absorb and separate dimethyl carbonate in the mixed gas by using methanol.

SUMMARY OF THE INVENTION

An object of the present invention is to provide an industrially advantageous continuous process for preparing dimethyl carbonate from carbon monoxide and methyl nitrite.

Another object of the present invention is to provide a process for separating dimethyl carbonate in a reaction gas mixture effectively and easily.

The present inventors have studied intensively in order to solve the above problems involved in the conventional separation methods, and as the results, they have established an industrially novel continuous process whereby accomplished the present invention.

That is, the present invention is a continuous process for preparing dimethyl carbonate which comprises the steps that:

a first step of introducing a gas containing carbon monoxide and methyl nitrite into a reactor filled with a solid catalyst carried thereon at least one of a platinum group metal and a compound thereof, or at least one of a platinum group metal and a compound thereof and a co-catalyst to effect catalytic reaction in a vapor phase to form a reaction product containing dimethyl carbonate;

a second step of separating the reaction product formed in the first step to a non-condensed gas containing nitrogen monoxide and a solution containing dimethyl carbonate by introducing the reaction product into an absorption column and adding dimethyl oxalate as an absorption solvent;

a third step of introducing the non-condensed gas of the second step into a regenerating column to contact it with a molecular state oxygen-containing gas and methanol whereby regenerating nitrogen monoxide in the non-condensed gas to methyl nitrite, so as to contain 2 to 7% by volume of nitrogen monoxide in a non-absorbed gas at an outlet of the column, which in turn is introduced in the reactor of the first step;

a fourth step of extracting, distilling and separating dimethyl carbonate from the solution containing dimethyl carbonate, methanol and dimethyl oxalate obtained in the second step by further adding dimethyl oxalate to remove methanol; and a fifth step of distilling and separating dimethyl carbonate from a mixed solution containing dimethyl carbonate and dimethyl oxalate obtained in the fourth step to remove dimethyl oxalate and recycling the removed dimethyl oxalate to the fourth step.

Also, the present invention relates to a process for preparing dimethyl carbonate which comprises synthesizing dimethyl carbonate from carbon monoxide and methyl nitrite in a vapor phase reaction in a column, the improvement wherein dimethyl oxalate is added to the column as an absorption solvent to absorb dimethyl carbonate for separating dimethyl carbonate from a reaction gas containing (1) a high boiling point reaction product mainly comprising dimethyl carbonate, and (2) a gas containing unreacted carbon monoxide, methyl nitrite and nitrogen monoxide.

In the present invention, by contacting a mixed gas containing dimethyl carbonate with dimethyl oxalate, dimethyl carbonate can be effectively absorbed to dimethyl oxalate under mild conditions while depressing methanol concentration at a low degree.

DESCRIPTION OF THE PREFERRED EMBODIMENTS

Figure 1:
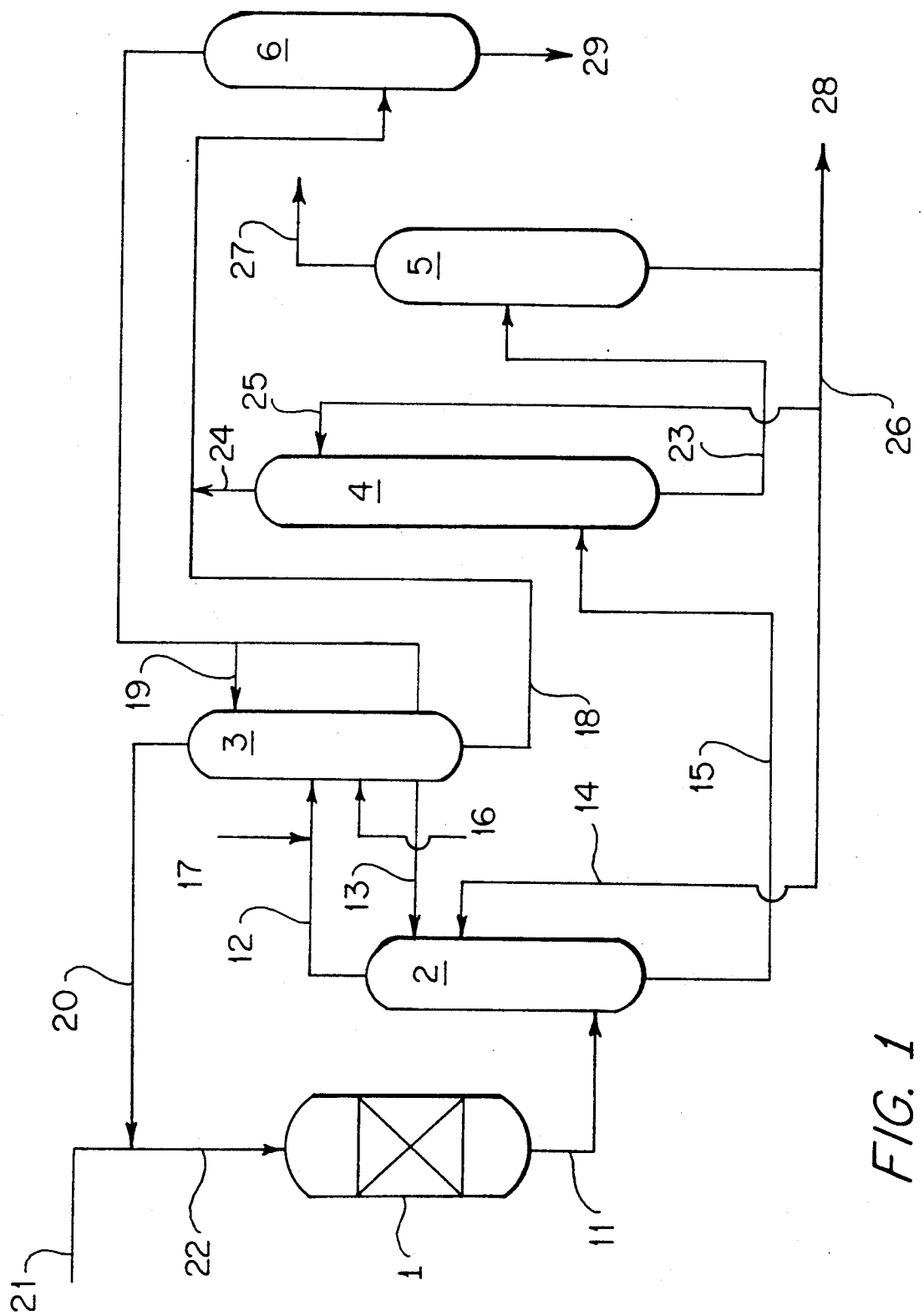
FIG. 1 is a processing diagram of the continuous preparation process showing one embodiment of the invention.

In the following, the present invention is to be described in more detail.

First step

A gas containing carbon monoxide and methyl nitrite is introduced into a reactor filled with a solid catalyst carried thereon a platinum group metal and/or a compound thereof, or a platinum group metal and/or a compound thereof and a co-catalyst to effect catalytic reaction in a vapor phase. As the reactor, single tubular system or multi-tubular system catalyst-filled column is effective. A contact time of the platinum group metal solid catalyst and starting gases is preferably set 10 seconds or shorter, more preferably 0.2 to 5 seconds. As the platinum group metal solid catalyst, effective are a catalyst in which platinum group metal compounds described in Japanese Provisional Patent Publication No. 141243/1991 are carried on a carrier, a catalyst in which a cation of the platinum group metal is carried on a carrier, and a catalyst in which a salt of copper or iron is added to the above catalyst as a co-catalyst or promoter.

As the carrier, activated charcoal, silica, diatomaceous earth, zeolite and clay mining are used. Also, a gas containing carbon monoxide and methyl nitrite, which is a starting gas, is generally diluted by a gas inert to the reaction such as nitrogen or carbon dioxide gas.

The reaction proceeds at a low temperature sufficiently and smoothly, and less side reaction occurs at a lower reaction temperature. Thus, the reaction is preferably carried out at a temperature as low as possible so long as a desired space time yield (STY) can be maintained, i.e. at 50° to 200° C., more preferably at 80° to 150° C. Also, the reaction is preferably carried out at a pressure of a normal pressure (about 0 kg/cm² (gauge pressure)) to 10 kg/cm² (gauge pressure), more preferably a normal pressure to 5 kg/cm² (gauge pressure), and some instances, the pressure may be slightly lower than the normal pressure.

A concentration of methyl nitrite in the starting gas may vary with a wide range, and in order to obtain satisfactory reaction rate, it is necessary to set the concentration to 1% by volume or more. However, a high concentration of methyl nitrite is not preferred in view of safety since methyl nitrite is an explosive compound so that the concentration range is preferably 3 to 25% by volume based on the starting gas. A concentration of carbon monoxide in the starting gas may also vary with a wide range and suitably be selected in the range of 10 to 90% by volume based on the starting gas. In a continuous process, since part of a circulating gas is purged from the system in order to maintain the concentration of an inert gas constantly, when the concentration is made high, loss of the starting gas out of the system becomes remarkable so that it is economically preferred to effect the reaction with the carbon monoxide concentration of 5 to 30% by volume based on the starting gas.

Second step

The reaction product formed in the first step is led to a bottom portion of an absorption column at which gas separation is carried out, and simultaneously, at the top portion of the absorption column, dimethyl oxalate is fed to absorb and separate dimethyl carbonate in the reaction gas by dimethyl oxalate. In a gas from which dimethyl carbonate is separated, a small amount of dimethyl carbonate and dimethyl oxalate are accompanied by and they are all becoming loss by hydrolysis at the third step for regenerating nitrogen monoxide. Thus, in order to recover dimethyl carbonate and dimethyl oxalate to be accompanied by, it is preferred to feed a small amount of methanol from the top portion of the absorption column.

An amount of dimethyl oxalate to be flown may vary depending on an amount of dimethyl carbonate to be incorporated into the absorption column, but suitably 3 to 10-fold weight, more preferably 4 to 6-fold weight based on the weight of dimethyl carbonate. Also, an amount of methanol to be fed from the top portion of the column is preferably as little as possible since methanol itself should be removed at the fourth step, but it is too little, losses of dimethyl carbonate and dimethyl oxalate become remarkable. Thus, it is suitably 5 to 30% by weight, more preferably 10 to 20% by weight based on the amount of dimethyl carbonate in the reaction gas.

An operation temperature of the absorption column is preferably as low as possible in order to carry out absorption of dimethyl carbonate effectively, but it is too low, dimethyl oxalate is solidified and it is disadvantageous in view of energy burden. Thus, it is suitably carried out in the range of 0° C. to 80° C., more preferably 10° C. to 50° C. A mixed solution of dimethyl carbonate and dimethyl oxalate separated by dimethyl oxalate is transferred to the fourth step in order to remove methanol and a small amount of a low boiling point compound such as methyl formate formed by the reaction. On the other hand, the non-condensed gas contains, in addition to nitrogen monoxide formed by the catalytic reaction at the first step, unreacted carbon monoxide and methyl nitrite, and transferred to the third step.

Third step

The non-condensed gas of the second step is introduced into a regenerating column to contact it with a molecular state oxygen-containing gas and methanol whereby regenerating nitrogen monoxide in the gas to methyl nitrite. As the regenerating column at this step, usual vapor-liquid contacting apparatuses such as a filled column, a bubble tower, a spray column and a plate column may be used.

The non-condensed gas and the molecular state oxygen-containing gas to be contacted with methanol may be introduced in the regenerating column separately or a mixed state. In the regenerating column, part of nitrogen monoxide is oxidized to nitrogen dioxide by the molecular state oxygen-containing gas, and they are absorbed to and reacted with methanol to regenerate methyl nitrite. As the molecular state oxygen-containing gas, pure oxygen gas or oxygen diluted by an inert gas may be used, and it is fed so as to become nitrogen monoxide concentration in the regenerated gas being 2 to 7% by volume. When the regenerated gas is used by circulating to the reactor of the first step, if the concentration of nitrogen monoxide exceeds 7% by volume, it remarkably inhibits the reaction, whereas if it is less than 2% by volume, significant amounts of oxygen and nitrogen dioxide are contained in the regenerated gas, which lower activity of the catalyst.

Thus, it is preferred that the molecular state oxygen-containing gas is supplied to in an amount of 0.08 to 0.2 mole per mole of nitrogen monoxide in the gas to be introduced into the regenerating column and these gases are contacted with methanol at a temperature of 60° C. or lower with a contact time of preferably 0.5 to 2 seconds. An amount of methanol to be used is an amount necessary for completely absorb and react nitrogen dioxide formed and substantially the equivalent mole of nitrogen monoxide, or more. Methanol is generally and preferably used in an amount of 2 to 5 mole per mole of nitrogen monoxide in the gas to be introduced into the regenerating column.

Since the present invention is a continuous process, methyl nitrite is expelled out of the system by dissolving in the absorption solution in the absorption column or a can solution in the regenerating column or part of the circulating gas is purged so that nitrogen oxide components are lost. Therefore, methyl nitrite may be supplemented to the reactor of the first step, or nitrogen oxide such as nitrogen monoxide, nitrogen dioxide, dinitrogen trioxide and dinitrogen tetroxide or nitric acid is supplemented to the regenerating column at the third step.

Also, when a content of nitrogen monoxide in the non-condensed gas at the second step is much and methyl nitrite with a larger amount than that of required is obtained at converting nitrogen monoxide into a nitrite, part thereof may be directly circulated to the reactor of the first step without leading to the whole amount of the non-condensed gas. A solution led out from the regenerating column is a methanol solution containing water which is by-produced by the regenerating reaction so that it is industrially advantageous to use again at the second step or the third step after purifying it to the water content in methanol of suitably 2% by volume or less, more preferably 0.2% by volume or less.

Fourth step

A mixed solution of dimethyl carbonate, methanol and dimethyl oxalate led out from the second step is fed to the bottom portion of an extraction and distillation column in order to remove methanol. At the same time, to the extraction and distillation column is newly fed dimethyl oxalate from the top portion of the column in order to prevent azeotropic phenomenon of methanol and dimethyl carbonate. An amount of dimethyl oxalate to be fed is suitably 0.1 to 2-fold mole based on the total mole of dimethyl carbonate and methanol to be fed to the column, preferably 0.5 to 1.5-fold mole. Dimethyl oxalate has a role of an absorbing agent which is important for preventing substantial loss of dimethyl carbonate to a distillation side, and an amount of dimethyl oxalate is defined by a number of steps of the distillation column for separation and an amount of energy to be used at separation. That is, if an amount of dimethyl oxalate is too small, loss of dimethyl carbonate to the distillation side becomes remarkable whereby an yield will worsen and number of steps of the absorption column required to be high. To the contrary, even if too much amount of dimethyl oxalate is flown, an effect of preventing loss of dimethyl carbonate to the distillation side cannot be obtained in proportion to the amount added and energy loss will be caused since the loss of dimethyl carbonate substantially stops when a predetermined amount of dimethyl oxalate is added.

An operational pressure is not particularly limited and the operation can be carried out with a wide range from a reduced pressure to under pressure, but preferably in the range of a normal pressure (about 0 kg/cm$^2$G) to 2 kg/cm$^2$G (guage pressure). Methanol distilled out from the extraction and distillation column is, as an industrial process, preferably used again at the second step or the third step. However, methyl formate or methylal which are by-produced in the reaction at the first step with a small amount is contained the methanol distilled, so that the methanol is preferably used again after removing these by-produced compounds by distillation. Incidentally, distillation residues such as methyl formate and methylal are disposed by burning up, but they can recover as methanol by decomposing with an alkali. A can solution remained at the bottom of the extraction and distillation column is transferred to the fifth step in the state of a solution containing two components of dimethyl carbonate and dimethyl oxalate.

Fifth step

A solution from which low boiling point products such as methanol and others are removed in the fourth step is transferred into a distillation column of the fifth step, at which dimethyl carbonate is distilled and separated therefrom and high quality dimethyl carbonate can be taken out continuously. An operational pressure is not particularly limited and the operation can be carried out with a wide range from a reduced pressure to under pressure. On the other hand, from a can solution of the distillation column of this fifth step, a significantly high purity dimethyl oxalate can be obtained and it can be supplied as such to the second step and the third step. Dimethyl oxalate formed as a by-product by the reaction at the first step is taken out as a by-produced product. Since dimethyl oxalate itself has various uses, it may be further distilled and purified, if necessary, whereas it has high purity in the state of the can solution. The distillation column used in the fourth step and the fifth step may be used conventional ones such as a filling column and plate column.

In one of the preferred embodiments of the present invention, a process for separating dimethyl carbonate of the second step is described in detail below.

A process for separating dimethyl carbonate from the reaction mixture of carbon monoxide and methyl nitrite should be considered from a global view point including treatment of methanol since, after separation, further separation from methanol, and distillation and purification should be effected as described above. That is, as for the process for separating methanol from a mixture of dimethyl carbonate and methanol, there are a method in which extraction and distillation are carried out by using dimethyl oxalate as disclosed in Japanese Patent Application No. 57696/1991 (which corresponds to European Patent Application No. 92 103 454.2), a method of using water as disclosed in Japanese Patent Publication No. 17333/1981, a method of using benzene or hydrocarbon, and a method of removing azeotropic phenomenon by pressurizing. However, even when either of the method is used, it is advantageous if an amount of methanol to be taken in is as little as possible in view of energy burden. Accordingly, it is necessary to reduce a methanol concentration after separation as well as improving recovery of dimethyl carbonate.

On the other hand, in order to separate dimethyl carbonate from the reaction mixture only by using methanol, a significant amount of methanol is required in order to heighten recovery of dimethyl carbonate and also high step number and cooling are required. For example, if one wishes to make a recovery of dimethyl carbonate from the reaction mixture 98% or more, the obtained mixture of dimethyl carbonate and methanol is required to have a methanol concentration of 50% by weight or more.

To the contrary, when dimethyl oxalate is used as an absorbing solvent as in the present invention, it is extremely easy to make a ratio of methanol to dimethyl carbonate 20% or less with a recovery of dimethyl carbonate being 99% or more. Also, dimethyl oxalate itself is circulated through separation from methanol in the next step and through the distillation and purification step, but usually exists at a can solution side whereby energy loss is extremely little so that the method is, as a whole, advantageous one in view of energy burden.

As an apparatus for separating dimethyl carbonate from the reaction mixture, usual filling column or plate column may be used, and they may be 5 to 7 plates or so in number of theoretical plates which may vary depending on a reaction gas composition and a flow amount thereof.

As operational conditions, the reaction gas is fed from the upper portion to the lower plate of the absorption column, dimethyl oxalate is fed from 2 to 3 plates from the top and a little amount of methanol is fed from the top portion in order to prevent loss of dimethyl oxalate accompanied by a gas. A flow amount of dimethyl oxalate may vary depending on the operational temperature and pressure, and on a desired recovery of dimethyl carbonate, but preferably 3-fold weight or more based on the amount of dimethyl carbonate in the reaction gas, more preferably 4-fold weight or more. Here, an amount of 3-fold weight gives a recovery of 98% or more and that of 4-fold weight gives a recovery of 99% or more. Even when the amount is made too large, it is not effective and loss of dimethyl oxalate into the gas increases so that 4 to 6-fold weight is particularly preferred.

Also, a flow amount of methanol is preferably as little as possible, but it is too little, a recovery of dimethyl carbonate decreases and loss of dimethyl oxalate into the separated gas increases. Thus, it is preferably 5 to 30% by weight, more preferably 10 to 20% by weight.

An operational temperature of the column largely affects to the recovery of dimethyl carbonate and it is preferably as low as possible. In the operation under the above conditions, only the top portion of the column may be slightly cooled by circulation to the column top temperature preferably in the range of 0° to 50° C., more preferably 10° to 30° C.

Also, as for pressure, it is not particularly limited in view of extracting effect of dimethyl oxalate, but it is preferably close or the same with the reaction pressure since the reactor is a series of an apparatus of the process. It is preferably carried out at slightly pressurized condition of 1 to 5 kg/cm$^2$G, more preferably 1 to 3 kg/cm$^2$G.

Next, the process of the present invention is explained in detail by referring to a flow sheet chart shown in FIG. 1 which shows one embodiment of the present invention.

A gas containing carbon monoxide, methyl nitrite and nitrogen monoxide is introduced into the upper portion of a multi-tubular system reactor 1 in which a platinum series metal solid catalyst is filled in a reactor through a pipe by pressurizing with a gas circulating machine (not shown) provided at a pipe 20. Catalytic reaction in vapor phase is carried out at the reactor 1, and a gas passed through the catalytic layer and formed by the reaction is taken out from the bottom portion of the reactor 1 and introduced into an absorption column 2 through a pipe 11.

At the absorption column 2, dimethyl carbonate in the gas formed by the reaction is contacted with methanol and dimethyl oxalate provided from pipes 13 and 14, respectively, to absorb it to dimethyl oxalate for separation, and a solution comprising dimethyl carbonate, dimethyl oxalate and methanol is introduced into an extraction and distillation column 4 from the bottom portion of the column 2 through a pipe 15. On the other hand, a non-condensed gas containing unreacted carbon monoxide and methyl nitrite, as well as a by-produced nitrogen monoxide and others is introduced to the bottom portion of a regenerating column 3 from the upper portion of the column 2 through a pipe 12.

At the regenerating column 3, the non-condensed gas is mixed with a molecular state oxygen-containing gas which is introduced to the bottom portion of the regenerating column 3 through a pipe 16 and the mixture is reacting with methanol introduced from the upper portion of the regenerating column 3 through a pipe 19 by countercurrent contact reaction to form methyl nitrite. In the regenerating column 3, subsequent to oxidation reaction of nitrogen monoxide to nitrogen dioxide, absorption reaction into methanol occurs and methyl nitrite is formed. When a nitrogen source sufficient for forming methyl nitrite is lacked, nitrogen oxide(s) may be mixed through a pipe 17.

A non-absorbed gas containing methyl nitrite formed at the regenerating column 3 is in turn supplied to the reactor 1 by circulation with newly supplied carbon monoxide from a pipe 21 through pipes 20 and 22. On the other hand, water by-produced at the regenerating column 3 is taken out from the bottom portion of the column 3 in the form of an aqueous methanol solution through a pipe 18. This aqueous methanol solution can be circulated and utilized again as a methanol supplied to the absorption column 2 or the regenerating column 3 through the above pipes 13 or 19 after removing water content in the solution by operations such as distillation.

At the extraction and distillation column 4, extraction only of dimethyl carbonate is carried out by countercurrent contact with dimethyl oxalate introduced thereinto through a pipe 25 to separate it from methanol. The separated methanol. The separated methanol is introduced into a distillation column 6 at which methanol purification is carried out from the upper portion of the column 4 through a pipe 24. After effecting purification, methanol is circulated and utilized again as a methanol supplied to the absorption column 2 and the regenerating column 3 through the above pipes 13 and 19, respectively. A mixed solution of dimethyl carbonate and dimethyl oxalate from which methanol is removed is led to a distillation column 5 through a pipe 23.

At the distillation column 5, dimethyl carbonate is obtained as a final product from the upper portion of the column 5 through a pipe 27. The remaining can solution is dimethyl oxalate with high purity and part thereof can be obtained as a by-product through a pipe 28, but the remaining are supplied to the absorption column 2 and the distillation column 4 through pipes 26, 14 and 25, respectively.

EXAMPLES

In the following, the process of the present invention is explained specifically by referring to Examples, but they are one of the embodiments of the present invention and the present invention is not limited by these Examples.

EXAMPLE 1

In a tube of a multi-piping reactor made of stainless steel having 6 tubes, an inner diameter of 26.1 mm and a height of 500 mm was filled 780 g (1.73 $\iota$, of a catalyst in which palladium is carried on an activated charcoal (available from K.K. Takeda, Japan, Shirasagi 4 mm$\phi \times$6 mm, trade name) as disclosed in Japanese Patent Application No. 257042/1990. To the upper portion of the catalyst layer was supplied a starting gas (composition: 15.0% by volume of carbon monoxide, 15.0% by volume of methyl nitrite, 3.5% by volume of nitrogen monoxide, 1.8% by volume of methanol, 2.2% by volume of carbonic acid gas and 62.5% by volume of nitrogen) previously pre-heated to about 90° C. by a heat-exchanger and compressed by a diaphragm type gas circulating pump to 2.5 kg/cm$^2$ (gauge pressure) with a rate of 6.9 Nm$^3$/hr, and a temperature at the center portion of the catalyst layer was maintained at about 120° C. by passing a hot-water through a shell side of the reactor. The reaction rate of forming dimethyl carbonate by the reaction was STY of 430 kg/m$^3$hr.

The gas passed through the catalyst layer was introduced into the bottom portion of a Raschig ring filled type vapor-liquid contact absorption column having an inner diameter of 100 mm and a height of 1300 mm, and methanol was introduced therein at the top of the column with a rate of 0.21 $\iota$/hr and dimethyl oxalate was introduced therein at the portion 200 mm below the top of the same with a rate of 2.65 kg/hr to effect countercurrent contact with a top column temperature of 5° C. and a bottom column temperature of 20° C. From the bottom of the absorber, 2.8 kg/hr of an absorbed solution (composition: 76.7% by weight of dimethyl oxalate, 19.6% by weight of dimethyl carbonate, 3.7% by weight of methanol and 0.1% by weight of methyl formate) was obtained. On the other hand, from the top of the column, 6.8 Nm$^3$/hr of a non-condensed gas (composition: 12.8% by volume of carbon monoxide, 10.3% by volume of methyl nitrite, 8.7% by volume of nitrogen monoxide, 1.9% by volume of methanol, 2.2% by weight of carbonic acid gas and 64.0% by volume of nitrogen) was obtained.

After the non-condensed gas was mixed with 87.2 N$\iota$/hr of oxygen and 7.5 N$\iota$/hr of a nitrogen gas containing 14.0% by weight of nitrogen monoxide, and then introduced into a vapor-liquid contact type regenerating column from the bottom portion thereof. From the top portion thereof, methanol was introduced with a rate of 5.0 $\iota$/hr to effect countercurrent contact with a top column temperature of 30° C. and a bottom column temperature of 20° C. 6.6 Nm$^3$/hr of a regenerated gas (composition: 12.8% by volume of carbon monoxide, 15.4% by volume of methyl nitrite, 3.7% by volume of nitrogen monoxide, 1.9% by volume of methanol, 2.3% by volume of carbonic acid gas and 64.1% by volume of nitrogen) at the regenerating column was supplied to the above gas circulating pump and condensed. Then, 0.2 Nm$^3$/hr of carbon monoxide was supplied to the compresseed regenerated gas and the mixed gas was introduced into the reactor. On the other hand, 4.0 $\iota$/hr of methanol containing 2.2% by weight of water led out from the regenerating column was used again as a methanol source in said column after removing water by distillation.

The absorbed solution in an amount of 3.5 kg/hr led out from the above absorption column was led to the middle step of a distillation column having an inner diameter of 50 m and a height of 2500 mm, and 1.4 kg/hr of liquid dimethyl oxalate was introduced therein at the position 300 mm below from the top of the column and distillation was carried out with a top column temperature of 64° C. and a bottom column temperature of 146° C. From the bottom of the column, 4.78 kg/hr of a mixed solution containing 14.3% of dimethyl carbonate and 87.5% by weight of dimethyl oxalate was obtained. On the other hand, from the top of the column, 0.13 kg/hr of a distilled solution comprising 94.5% by weight of methanol, 5.2% by weight of methyl formate and 0.3% by weight of dimethyl carbonate was obtained. The distilled solution was circulated and used again in the above regenerating column and the absorption column after purification of methanol in a distillation column.

The mixed solution of dimethyl carbonate and dimethyl oxalate led out from the above distillation column was led to a filling column having an inner diameter of 65 mm and a height of 1600 mm, and distilled with a top column temperature of 90° C. and a bottom column temperature of 163° C. From the top of the column, 0.68 kg/hr of dimethyl carbonate with a purity of 99.4% was obtained. Also, from the bottom of the column, 4.69 kg/hr of dimethyl oxalate with a purity of substantially 100% was taken out, and 4.05 kg/hr thereof was circulated and supplied to the absorption column and the extraction and distillation column. As the results, from dimethyl carbonate formed by the reaction, high purity dimethyl carbonate can be obtained continuously with a formation yield of 98%.

EXAMPLE 2

At the bottom of an oldershow having an inner diameter of 32 mm and number of steps of 10, a one liter of a flask having was equipped and dimethyl oxalate was charged previously in the bottom flask by dissolving under heating. A reaction gas mixture was fed from a nozzle attached to the top of the flask with a rate of 1400 N$\iota$/hr and 400 g/hr of dimethyl oxalate dissolved solution was fed continuously from the fourth step from the top portion of the column. Also, from the top portion of the column, 15 g/hr of methanol was fed and a liquid was taken out from the third step from the top portion of the column and circulated to the top portion of the column through a cooler whereby the top portion of the column was cooled to 20° C.

A reaction gas containing dimethyl carbonate was obtained by passing carbon monoxide and methyl nitrite through a solid catalyst bed as shown in Japanese Provisional Patent Publication No. 141243/1991, and the composition of which is, at a temperature of 105° C., 1.75% by volume of dimethyl carbonate, 4.00% by volume of methanol, 0.13% by volume of dimethyl oxalate, 11.32% by volume of methyl nitrite, 11.74% by volume of carbon monoxide, 7.60% by volume of nitrogen monoxide, 0.10% by volume of methyl formate, 0.50% by volume of carbon dioxide and 63.00% by volume of nitrogen.

A liquid was taken out so as to become a liquid surface of the bottom flask constant (524 g/hr), and the operation was continued until inside of the column and bottom become a steady state. When the state becomes steady, a gas led out from the top of the column and the bottom solution were sampled and analyzed by using a gas chromatography. As the results, the composition of a gas led out from the top portion of the column was 0.01% by volume of dimethyl carbonate and 0.00% by volume of dimethyl oxalate, and that of the bottom solution was 18.70% by weight of dimethyl carbonate, 3.17% by weight of methanol, and 78.05% by weight of dimethyl oxalate.

A recovery of dimethyl carbonate was 99.5% and a ratio of methanol to dimethyl carbonate in a taken out solution was 0.17 (weight ratio).

EXAMPLE 3

In the same manner as in Example 2 except for changing a feeding amount of dimethyl oxalate to 300 g/hr. As the results, a recovery of dimethyl carbonate was 98.4%, and a ratio of methanol to dimethyl carbonate in the extracted solution was 0.17 (weight ratio).

EXAMPLE 4

In the same manner as in Example 2 except for changing a feeding amount of methanol to 5 g/hr. As the results, a recovery of dimethyl carbonate was 98.0%, and a ratio of methanol to dimethyl carbonate in the extracted solution was 0.06 (weight ratio).

COMPARATIVE EXAMPLE 1

In the apparatus used in Example 2, a liquid circulation for cooling was changed that a liquid was taken out from the bottom solution and the ninth step from the upper portion of the column to circulate to the seventh step, and the reaction gas mixture was fed in the same manner as in Example 2. From the top portion of the column, 100 g/hr of methanol was fed and the column was cooled so as to the bottom temperature of 20° C. and the ninth step temperature of 0° C., respectively. As the results, a recovery of dimethyl carbonate was 98.2% and a ratio of methanol to dimethyl carbonate in the extracted solution was 1.02 (weight ratio).

COMPARATIVE EXAMPLE 2

In the same manner as in Comparative example 1 except for changing a feeding amount of methanol to 24 g/hr. As the results, a recovery of dimethyl carbonate was 95.6%, and a ratio of methanol to dimethyl carbonate in the extracted solution was 0.24 (weight ratio).

According to the process of the present invention, when separating dimethyl carbonate from a mixed gas containing dimethyl carbonate formed by the reaction, by contacting the mixed gas with dimethyl oxalate, dimethyl carbonate can be effectively separated under mild conditions and obtained extremely economically as a whole while an amount of methanol to be co-presented can be depressed as little as possible. Thus, the process of the present invention can provide dimethyl carbonate continuously which is industrially extremely advantageous.

We claim:

1. A continuous process for preparing dimethyl carbonate which comprises:
    a first step of introducing a gas containing carbon monoxide and methyl nitrite into a reactor filled with a solid catalyst carried thereon at least one of a platinum group metal and a compound thereof, or at least one of a platinum group metal and a compound thereof and a co-catalyst to effect catalytic reaction in a vapor phase to form a reaction product containing dimethyl carbonate;
    a second step of separating the reaction product formed in the first step to a non-condensed gas containing nitrogen monoxide and a solution containing dimethyl carbonate by introducing the reaction product into an absorption column and adding dimethyl oxalate as an absorption solvent;
    a third step of introducing the non-condensed gas of the second step into a regenerating column to contact it with a molecular state oxygen-containing gas and methanol whereby regenerating nitrogen monoxide in the non-condensed gas to methyl nitrite, so as to contain 2 to 7% by volume of nitrogen monoxide in a non-absorbed gas at an outlet of the column, which in turn is introduced in the reactor of the first step;
    a fourth step of extracting, distilling and separating dimethyl carbonate from the solution containing dimethyl carbonate, methanol and dimethyl oxalate obtained in the second step by further adding dimethyl oxalate to remove methanol; and
    a fifth step of distilling and separating dimethyl carbonate from a mixed solution containing dimethyl carbonate and dimethyl oxalate obtained in the fourth step to remove dimethyl oxalate and recycling the removed dimethyl oxalate to the fourth step.

2. The process according to claim 1, wherein dimethyl oxalate is added in the second step in an amount of 3 to 10-fold weight per weight of dimethyl carbonate.

3. The process according to claim 1, wherein dimethyl oxalate is added in the second step in an amount of 4 to 6-fold weight per weight of dimethyl carbonate.

4. The process according to claim 1, wherein methanol is further added to the second step in an amount of 5 to 30% by weight based on the amount of dimethyl carbonate in the reaction product.

5. The process according to claim 4, wherein the second step is carried out at a temperature of 0° C. to 80° C.

6. The process according to claim 1, wherein the catalytic reaction at the first step is carried out at a temperature of 50° to 200° C. and at a pressure of normal pressure to 10 kg/cm$^2$ (gauge pressure).

7. The process according to claim 6, wherein the gas introduced in the first step comprises 3 to 25% by volume of methyl nitrite, 5 to 30% by volume of carbon monoxide and an inert gas as the reminder.

8. The process according to claim 1, wherein the molecular state oxygen-containing gas is added in the third step in an amount of 0.08 to 0.2 mole in terms of oxygen per mole of nitrogen monoxide and contacted with the non-condensed gas and methanol for 0.5 to 2 seconds.

9. The process according to claim 8, wherein methanol is added in the third step in an amount of 2 to 5 mole per mole of nitrogen monoxide in the non-condensed gas.

10. The process according to claim 1, wherein dimethyl oxalate is added in the fourth step in an amount of 0.1 to 2-fold mole per total molar number of dimethyl carbonate and methanol.

11. The process according to claim 1, wherein dimethyl oxalate is added in the fourth step in an amount of 0.5 to 1.5-fold mole per total molar number of dimethyl carbonate and methanol.

12. A process for preparing dimethyl carbonate which comprises synthesizing dimethyl carbonate from carbon monoxide and methyl nitrite in a vapor phase reaction in a column, the improvement wherein dimethyl oxalate is added to the column as an absorption solvent to absorb dimethyl carbonate for separating dimethyl carbonate from a reaction gas containing (1) a high boiling point reaction product mainly comprising dimethyl carbonate, and (2) a gas containing unreacted carbon monoxide, methyl nitrite and nitrogen monoxide.

13. The process according to claim 12, wherein dimethyl oxalate is added in an amount of 4 to 6-fold weight per weight of dimethyl carbonate.

14. The process according to claim 12, wherein methanol is further added in an amount of 5 to 30% by weight based on the amount of dimethyl carbonate in the reaction gas.

15. The process according to claim 12, wherein absorption is carried out at a temperature at the top of the column of 0° to 50° C. and a pressure in the column of 1 to 5 kg/cm$^2$G.

* * * * *